United States Patent [19]
Hok

[11] Patent Number: 5,195,528
[45] Date of Patent: Mar. 23, 1993

[54] ACOUSTIC RESPIRATION DETECTOR

[75] Inventor: Bertil Hok, Västerås, Sweden

[73] Assignee: Hok Instrument AB, Västerås, Sweden

[21] Appl. No.: 768,185

[22] PCT Filed: Feb. 13, 1991

[86] PCT No.: PCT/SE91/00099
§ 371 Date: Oct. 11, 1991
§ 102(e) Date: Oct. 11, 1991

[87] PCT Pub. No.: WO91/12051
PCT Pub. Date: Aug. 22, 1991

[30] Foreign Application Priority Data
Feb. 16, 1990 [SE] Sweden .................. 9000552

[51] Int. Cl.$^5$ ............................... A61B 5/08
[52] U.S. Cl. ........................... 128/716; 128/725; 128/204.23; 128/205.25
[58] Field of Search .............. 128/716, 724, 725, 848, 128/204.21, 204.23, 204.26, 205.23, 205.25

[56] References Cited
U.S. PATENT DOCUMENTS

| | | |
|---|---|---|
| 3,504,542 | 4/1970 | Blevins .................. 128/725 |
| 3,611,801 | 10/1971 | Paine .................. 128/716 |
| 4,438,772 | 5/1984 | Slavin . |
| 4,475,559 | 10/1984 | Horn . |
| 4,602,644 | 7/1986 | DiBenedetto et al. . |
| 5,005,571 | 4/1991 | Dietz .................. 128/205.25 |
| 5,052,400 | 10/1991 | Dietz .................. 128/204.26 |
| 5,074,299 | 12/1991 | Dietz .................. 128/204.26 |

FOREIGN PATENT DOCUMENTS 3707952 9/1988 Fed. Rep. of Germany .
2609623 7/1988 France .................. 128/725

OTHER PUBLICATIONS

M. Miyakawa et al.; Acoustic Measurement of the Respiratory System-An Acoustic Pneomograph; *Medical & Biological Engineering*, vol. 14, No. 6, pp. 653-659, Nov. 1976.

*Primary Examiner*—Lee S. Cohen
*Assistant Examiner*—Brian Casler
*Attorney, Agent, or Firm*—Watson, Cole, Grindle & Watson

[57] ABSTRACT

An acoustic respiration detector includes at least two tubular air transmission lines having ends which are connected to microphone elements. Close to the other ends of the lines are openings at which turbulence, and hence acoustic signals, are created by the incidence of airflow caused by respiration. A holding element secures the openings relative to the mouth or nose of a patient whose respiratory function is to be monitored, and a flow directing element, for example formed like a face mask, directs the airflow to the openings. The microphone elements are connected in a bridge circuit with two voltage supplying leads and at least one signal lead. Thereby the sensitivity to mechanical and acoustic disturbances is suppressed.

5 Claims, 2 Drawing Sheets

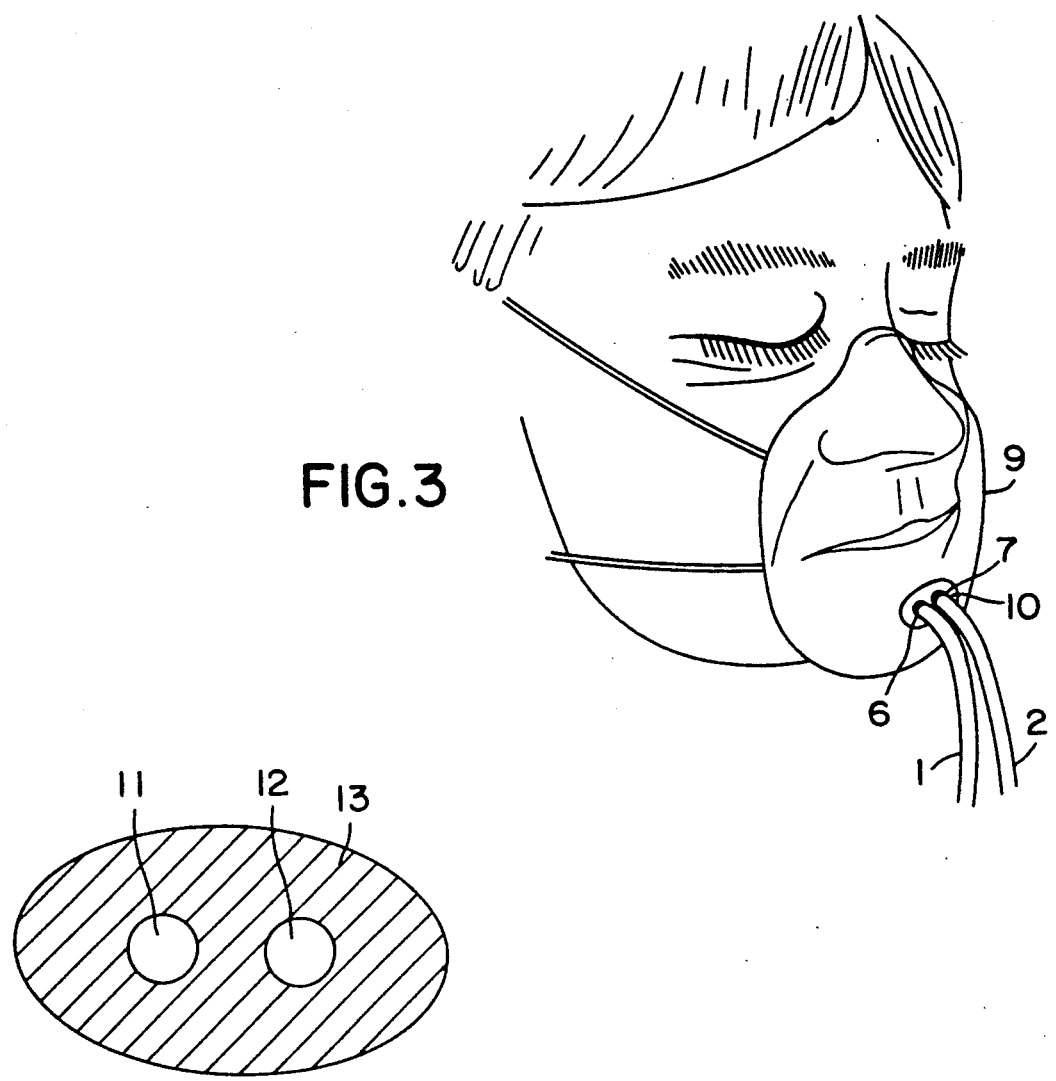
FIG. 3
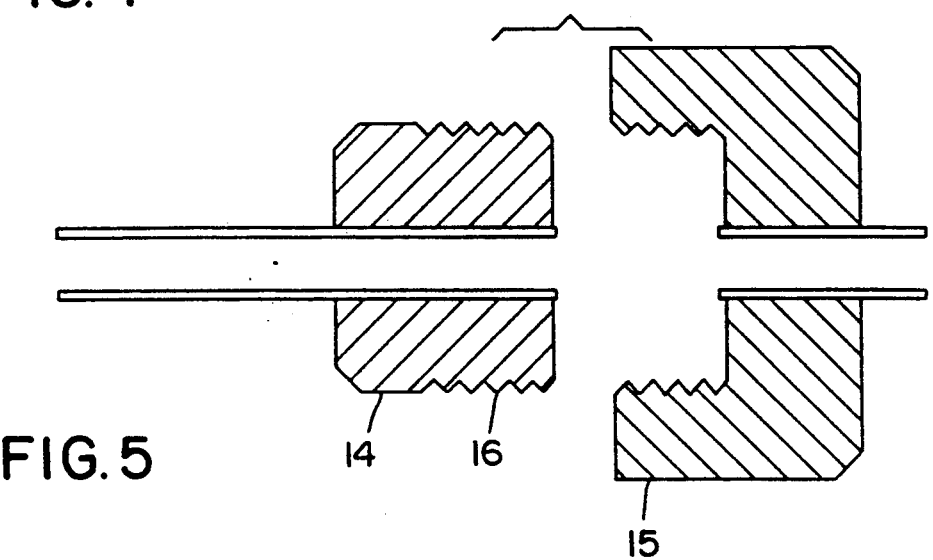
FIG. 4
FIG. 5

ACOUSTIC RESPIRATION DETECTOR

BACKGROUND OF THE INVENTION

In health care, it is often desirable to monitor respiration of a human being (or correspondingly, of an animal in veterinary medicine). For example, respiration is affected during anesthesia, since the respiratory centre of the brain is then brought is then brought out of function. Usually, the patient is mechanically ventilated during anesthesia, and is brought back to normal respiration during the wakening procedure. In this state of awakening, there is a risk of apnea (break arrest), which can be very traumatic and risky to the patient.

Further, it is known that the respiratory function of newborn babies sometimes is not fully developed, which can also lead to apnea, and in some cases to death (the so called sudden infant death syndrome). The direct causes of these tragic cases are still not sufficiently known, but there seems to be a consensus that apnea is the primary symptom, and that this may be easily heaved if it is discovered early enough.

From the cases mentioned above, it should be clear that monitoring respiration is highly important in certain groups of patients. The technological problem of detecting this function has, indeed, been he subject of several innovations and designs. One can classify these detectors into, on the one hand, those which record the respiratory motion of the patient, and on the other those which detect the flow of air resulting from respiration. The first kind could consist of a belt tied around the chest, with a sensor detecting the variations of length or tension caused by respiration motion. Alternatively, the so called transthoracid impedance is recorded with electrodes placed on the chest wall. Since the impedance is varying when the lungs are filled with air, or emptied, a signal is received which can be used for respiration monitoring.

Common to these methods of recording chest motion is, however, that they are sensitive also to other movements of the patient. This is especially serious, since it can give rise to a false negative response, i.e., the monitoring equipment records an artefact as the desired signal and does not give an alarm despite a possible breath arrest of the patient.

A detector of the flow of expired air does not have this serious limitation, since the detection principle is not coupled to the motion of the patient, given that the detector is fixed to the patient's mouth and nose in such a way that it is hit by the stream of air independently of the motion of the patient, and that the detector is protected from other sources of air flow, e.g., wind or draught.

Gas flow can be detected in several ways. The technical literature is dominated by variants of hot wire anemometer which is based on detection of the temperature change caused by the cooling effect of streaming gas on a heated body. For respiration detection one can make use of the fact that expired air is heated by the human body, making it very simple to place a sensitive temperature sensor in the air flow. This principle has, together with impedance measurements, become the dominant detection principle in clinical practice. It is, however, hampered by several drawbacks. For example, a fast response is required in order to to record single breaths. Therefore, only miniaturised temperature sensors, e.g. thermistors with extremely small mass, can be used. These are difficult to handle, since the very small connecting wires easily break. To guarantee patient safety against electric shocks, the sensor connections must be galvanically isolated from all other equipment, which requires expensive isolation amplifiers. Furthermore, drops of condensed water can develop on the sensor due to the high concentration of water vapor of expired air. Then the response of the sensor is altered, and its function as a respiration detector may be lost.

SUMMARY OF THE INVENTION

The invention described in this application solves these and other related problems in a satisfactory manner. The solution consists of acoustic detection of the expired gas. Thereby the general advantages by detecting expired air are fully exploited. Furthermore, the drawbacks, such as sensitivity to condensed water, are eliminated in the acoustic detection principle.

Several other advantages are also obtained. It is possible to physically separate the actual signal receptor function from the area of detection by acoustic signal transmission. The sensor, in this case a microphone, can be placed in a protected location inside an instrument housing.

The acoustic signal transmission takes place in an air transmission line, which simply consists of a length of plastic tubing. By using two, or more, microphone elements connected to one air transmission line each, and connected in a differentially amplifying circuit, it is possible to suppress other acoustic or mechanical signals which could otherwise disturb the desired function. Acoustic signal transmission in air transmission lines is well known. Of course, loss and standing wave phenomena occur in such lines, causing a spectral redistribution of the frequency contents of the signal. This is, however, of minor importance, since a respiration detector could, in general, be based on detection of the prevalence of a certain sound rather than specifying the quality of it.

The present acoustic respiration detector can be divided into one rugged instrument path with a long life, and a receptor part, having a very simple design and a low fabrication cost. The receptor part can then be a disposable item, which is motivated both for hygienic and economic reasons; re-use being more more labor intensive. The present invention is explained in more detail in the enclosed claims and FIG. drawings.

BRIEF DESCRIPTION OF THE DRAWINGS

FIGS. 2, 3, and 4 and 5 show detailed design examples.

DETAILED DESCRIPTION OF THE PREFERRED EMBODIMENTS

Figure 1:
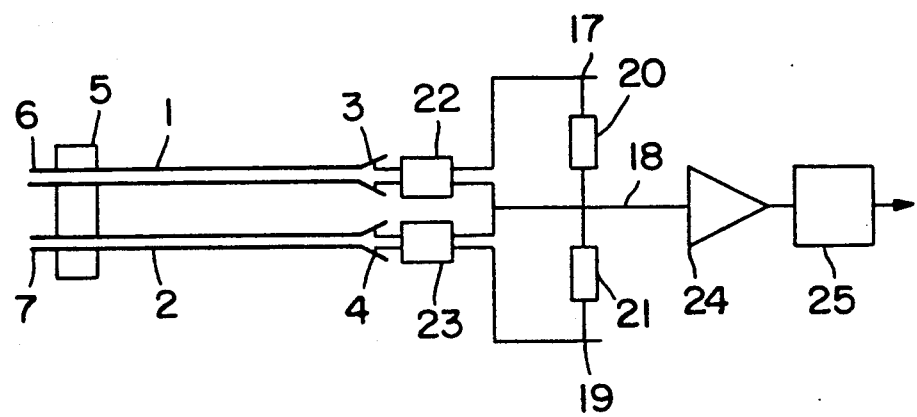
FIG. 1 shows the principal outline of the respiration detector according to the invention.

From the principal outline in FIG. 1, the tubular, cylindrical air transmission lines 1 and 2 are seen, connected at the ends 3 and 4 to microphone elements 22, 23. The microphone elements can, for example, be electric elements, i.e., condenser microphones with built-in polarisation and preamplifier. Miniature electric elements can commercially available from several manufacturers. The connection between the elements 22, 23 and the line ends 3, 4 should be leak-proof so that acoustic signals from the ambient are not picked up by the microphone element. The air transmission lines 1 and 2 can have a length of 50-300 cm and consist of flexible tubing of polyvinyl chloride, polyethylene, or the equivalent, with an inner diameter of 1–3 mm, and an outer diameter of 2–6 mm. The other ends 6, 7 of the lines 1, 2 are open and should be positioned in the flow of air caused by respiration. Fixation of the ends 6 and 7 is made with a holding element 5, which could, in the simplest case, be a piece of adhesive tape, but which could also have a more complex design and function. For example, the holding function can be performed by rubber bands tied around the patient's head. The openings 6, 7 of the lines 1, 2 do not need to be located at the end surface of the line but could be located along the mantle surface of the line. Furthermore, it must be pointed out that the openings 6, 7 only need to be open in an acoustic sense. It could, for example, be an advantage to provide these with a porous filter, a thin, flexible membrane, or the like, to prevent foreign particles and condensed water from blocking the acoustic signal transmission.

The microphone elements 22, 23 are connected in a bridge circuit with voltage supplying leads 17, 19 and a common signal transmitting lead 18. An amplifier 24 and a band pass filter 25 are connected to give the signal the required amplitude and noise immunity. In the bridge circuit, resistive or capacitive impedances 20, 21 can be incorporated to compensate for individual variations in sensitivity of the microphone elements 22, 23. In practice, this is done in such a way that the microphone elements are subjected to one and the same sound source, and the magnitude of the impedances 20, 21 are adjusted until the detector is sensitive to the momentary pressure difference between the microphone elements 22, 23, wherein the sensitivity to common acoustic noise is practically none at all.

A gas flow at the line ends 6, 7 gives rise to turbulence, and noise-like acoustic signals in the respective line ends 6,7 which are not correlated to each other. These uncorrelated signals will add according to $S=(S1+S2)^{\frac{1}{2}}$, where S1 and S2 are the signals in the respective line ends, and S the resulting signal, according to known signal theory, and therefore give rise to a net output signal from the signal lead 18 of the bridge circuit.

Figure 2:
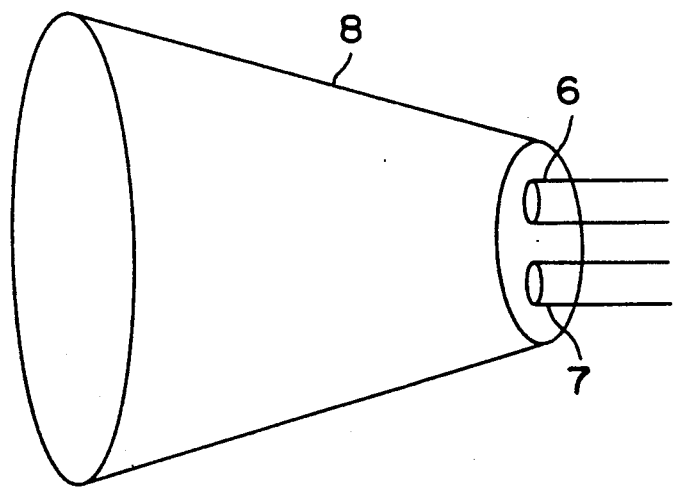

FIG. 2 shows a detailed picture of a design of the open ends of the air transmission lines 1, 2. Besides the holding element 5 there is also a flow directing element 8, designed to direct the steam of air caused by respiration towards the line ends 6, 7. Besides the flow directing function, this element may also concentrate the air flow by restricting it through a more narrow area. The flow directing element 8 can be designed in many possible ways. It is, for example, possible to use acoustic resonance phenomena by adapting its inner volume and its opening area. Such resonators, called Helmhoitz cavities, are well known in many musical instruments. Other types of resonators can also be built into the flow directing element, for example vibrating reeds, and other mechanical elements. The use of resonance phenomena has the advantage that the bandwidth of the signal is more limited, which makes it possible to choose a more narrow band pass filter 25. This in turn leads to further improved suppression of noise and disturbances.

The flow directing element 8, with or without an acoustic resonator function, can have the form of a face mask 9 as shown in FIG. 3. The face mask 9 covers both the mouth and the nose of the patient. Inspired and expired air passes through an opening 10, the area of which can be chosen so that a concentration of the air stream is obtained during passage through this opening 10. The flow directing element 8 can be advantageously be fabricated as a moulded plate of polymer, textile or cellulose-based material.

In FIG. 4 a special design of the air transmission lines 11, 12 built in a common polymer mantle 13, e.g., polyvinyl chloride or polyethylene, is shown. Each of the lines 11, 12 are connected in the same way as shown in FIG. 1 to a microphone element. The common mantle, or a corresponding mechanical coupling between the lines 11, 12, give the advantage of less sensitivity to mechanical disturbances in the form of movements of the lines. Since such movements in this case leads to identical noise signals in the lines 11, 12, there will be no net signal from the bridge circuit.

FIG. 5 shows a connector which can be incorporated into the air transmission lines 1, 2, 11, 12. The connector consists of two dismountable units 14 and 15, which by connection can be locked by threads 16. Alternative solutions, e.g., a bayonette lock, are, of course conceivable. Introducing connectors into the system means that the receptor part, eventually a disposable item, can be separated from the instrument part.

The acoustic respiration detector as deified by the enclosed claims can be given a highly variable detailed design using known technology.

I claim:

1. Detector of air flow at the respiratory organs of a human being or an animal including:
   at least two tubular air transmission lines positioned side by side, each defining an inner lumen and openings near or at opposite ends thereof,
   means for mechanically coupling said transmission lines,
   at least one microphone element acoustically connected to the inner lumen of each of said tubular air transmission lines,
   a bridge circuit having at least two voltage supply leads and at least one signal carrying lead connected to said microphone elements, and
   at least one holding element securing said air transmission lines such that said openings are exposed to said air flow.

2. Detector according to claim 1, wherein said bridge circuit includes resistive or capacitive impedance elements.

3. Detector according to claim 1, wherein at least one amplifier and at least one band pass filter are connected to the signal lead of said microphone elements.

4. Detector according to claim 1, wherein said air transmission lines are secured by the holding element in such a way that said openings are exposed to air flow from both the nostrils and the mouth of said human being or animal.

5. Detector according to claim 1, including means to lock said acoustic connection.

* * * * *